(12) United States Patent
Selby

(10) Patent No.: US 8,490,464 B1
(45) Date of Patent: Jul. 23, 2013

(54) TESTING FOR GAS IN LIQUID

(76) Inventor: Theodore W. Selby, Midland, MI (US)

( * ) Notice: Subject to any disclaimer, the term of this patent is extended or adjusted under 35 U.S.C. 154(b) by 646 days.

(21) Appl. No.: 12/657,490

(22) Filed: Jan. 21, 2010

Related U.S. Application Data

(60) Provisional application No. 61/205,658, filed on Jan. 22, 2009, provisional application No. 61/278,370, filed on Oct. 6, 2009.

(51) Int. Cl.
*G01N 33/26* (2006.01)

(52) U.S. Cl.
USPC .......... 73/19.1; 73/60.11; 73/61.41; 73/19.11

(58) Field of Classification Search
USPC .................................. 73/19.11, 61.41, 60.11
See application file for complete search history.

(56) References Cited

U.S. PATENT DOCUMENTS

| | | | | |
|---|---|---|---|---|
| 5,824,886 | A | 10/1998 | Selby et al. | 73/60.11 |
| 6,009,748 | A | 1/2000 | Hildebrandt et al. | 73/60.11 |
| 6,477,886 | B1 * | 11/2002 | Colvin et al. | 73/19.05 |
| 7,033,975 | B2 * | 4/2006 | Baran et al. | 507/102 |
| 2009/0088485 | A1 * | 4/2009 | Van Dijk et al. | 516/115 |

OTHER PUBLICATIONS

Selby, U.S. Appl. No. 61/205,658, filed Jan. 22, 2009 A.D., entitled, "Foam and Aeration-gas Entrainment Test Method and Apparatus."
Selby, U.S. Appl. No. 61/278,380, filed Oct. 6, 2009 A.D., entitled, "Engine Oil Air Entrainment and Release."
ASTM D 892-06, "Foaming Characteristics of Lubricating Oils."
ASTM D 6082-03, Evaluation of Aeration Resistance of Engine Oils in Direct-Injected Turbocharged Automotive Diesel Engine.
Hodges, P., "Hydraulic Fluids," John Wiley and Sons, 1996, Chapter 7, "Compressibility," page Nos. 55-66, incl. 59-61.
Williams, L., "Aeration," Transcription of audio in audiovisual clip, GF-5 Video Archives (www.gf-5.com), 2008, Lubrizol.
Choi, J-K et al., SAE Paper No. 932785, Effect of Oil Aeration Rate on the Minimum Oil Film Thickness and Reliability of Engine Bearing, given Oct. 18-21, 1993, Philadelphia, Pa.

(Continued)

*Primary Examiner* — Hezron E Williams
*Assistant Examiner* — Paul West
(74) *Attorney, Agent, or Firm* — Christopher John Rudy

(57) ABSTRACT

Liquid, say, an oleaginous liquid or an ink, for example, an engine oil, can be tested for aeration, entrainment and/or dissolution of a gas and/or foaming. The liquid can be tested through generation of a foam, for example, through aeration with employment of a vacuum, which can be carried out at a controlled, elevated temperature, for example, about 150° C., and the foam measured as to volume generated; and/or by testing for an entrained/dissolved gas directly, say, by drawing off the entrained/dissolved gas with a high vacuum, which can be done following aeration, for example, at a moderate temperature, for example, about 30° C. The gas can be air. Apparatus for use in such testing can include an outer, selectively sealable tube, which can be transparent, and which can serve as a vessel to contain a sample of a liquid as aforesaid to be tested; and, within the outer tube, a smaller generally vertical, inner tube also extending upward from and optionally out of the sealed outer tube. The smaller, inner tube is tipped at its bottom with an outlet capable of releasing a gas into the liquid sample, which may be released in a form of fine bubbles. The apparatus may be further provided with a contrivance for measuring contents of the sample within the outer tube and/or with a volume measuring device for ascertaining volume of released gas without generation of foam.

14 Claims, 12 Drawing Sheets

OTHER PUBLICATIONS

Nikolajsen, J., *Tribology Transactions*, vol. 42(1), 1999, pp. 189-191, "Viscosity and Density Models for Aerated Oil in Fluid-Film Bearings."

Chun, S., *Tribology International*, vol. 35, 2002, pp. 1-13, "A Parametric Study on Bubbly Lubrication of High-Speed Journal Bearings."

Jang, S. et al., *International Journal of Automotive Technology*, vol. 6(4), 2005, pp. 421-427, "Study on the Effect of Aerated Lubricant on the Journal Traces in the Engine Bearing Clearance."

Porot, P. et al., SAE Paper No. 930997, "A Numerical and Experimental Study of the Effect of Aeration of Oil on Valve Trains Equipped with Hydraulic Lash Adjusters," 1993.

King, T., ILSAC/Oil Chairman, Comments, 2009.

ASTM D 6894-03, Evaluation of Aeration Resistance of Engine Oils in Direct-Injected Turbocharged Automotive Diesel Engine.

Linden, J., General Motors, Samples for Tests, Dec. 2008 A.D.

Linden, J. et al/aux, Comments, Warren, Mich., Feb. 2009 A.D.

Selby, T., SAE International No. 09SFL-0341, 2008, published in May of 2009, entitled, "Engine Oil Air Entrainment and Release—Preliminary Studies," 8 pp.

Selby, T. et al., "A New Approach to the Determination of Extracted Pro-foamants from Elastomeric Sealants," Paper Presented at 12th Esslingen Colloquium, Jan. 11-13, 2000, Esslingen, Germany, 8 pp.

Savant, Inc., Midland, MI, Lubrication Technology Newsletter, Sep. 1996, pp. 1 and 4, "Foam testing now available."

Tannas Co., Midland, MI, Technical Bulletin No. 4, Dec. 1996, pp. 1-2, "Tannas Foam Air Bath (TFAB)."

Tannas Co., Midland, MI, Tannas Update, Fall 1998, p. 6, "Tannas Foam Test Equipment Increases safety, efficiency."

\* cited by examiner

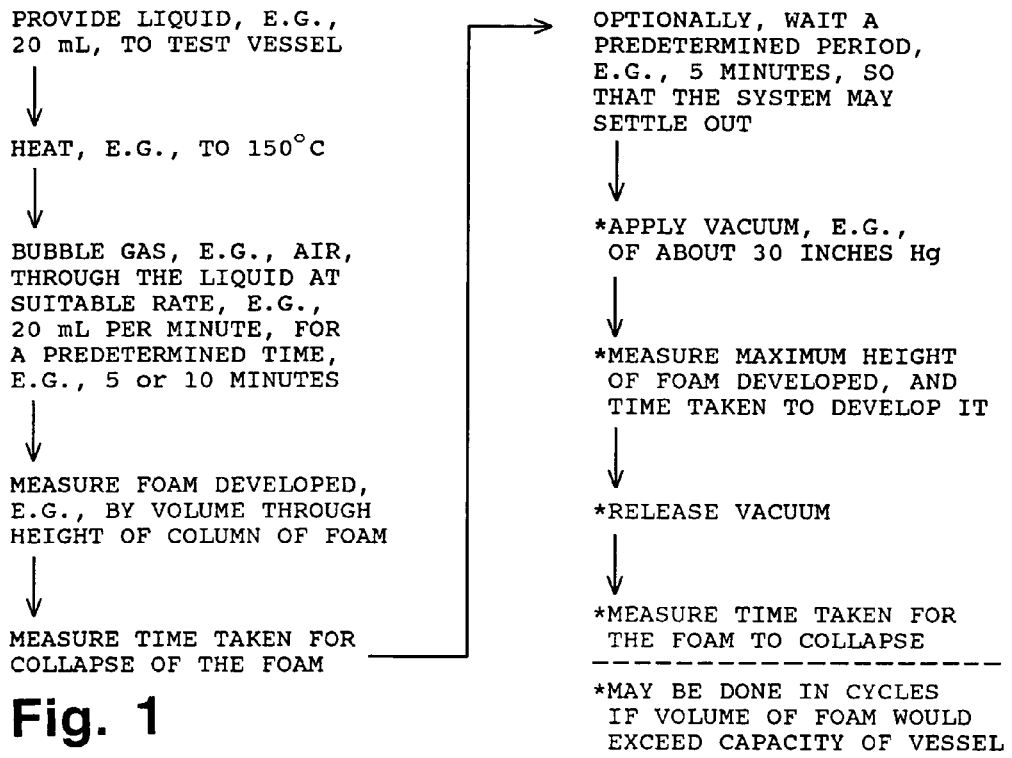
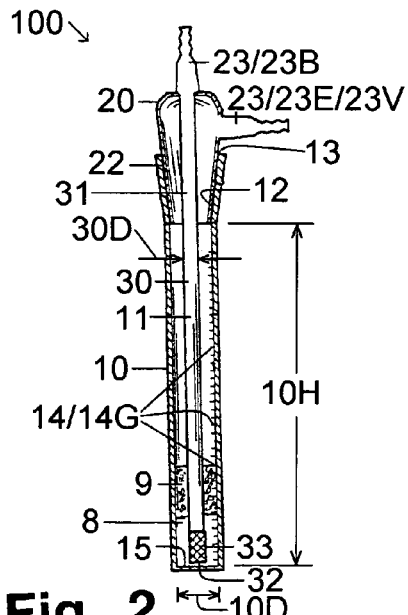
Fig. 2
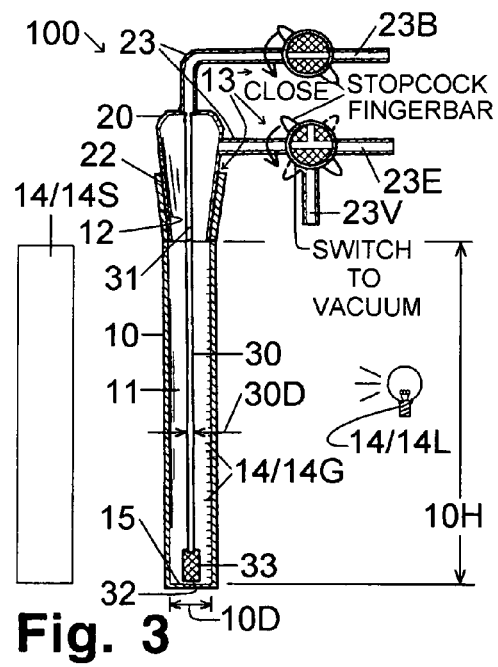
Fig. 3

Figure 6- Aeration (foaming) results with Protocol A1

Figure 7 - Volume of entrained air released

Figure 8 - Total foam volume and foam collapse time during aeration at atmospheric pressure Figure 9 - Progressively summed foam volumes released from entrained and dissolved air in vacuum tests Figure 10 - Volume of foam generated from the Protocol A2 tests on air-saturated engine oils Figure 11 - Time of sequential foam formation from the air-saturated test oils Figure 12 - Rate of sequential foam formation from the air-saturated test oils Figure 13 - Collapse time of sequential foam formation from the air-saturated test oils Figure 14 - Collapse rate of sequential foam formation from the air-saturated test oils Fig. 15
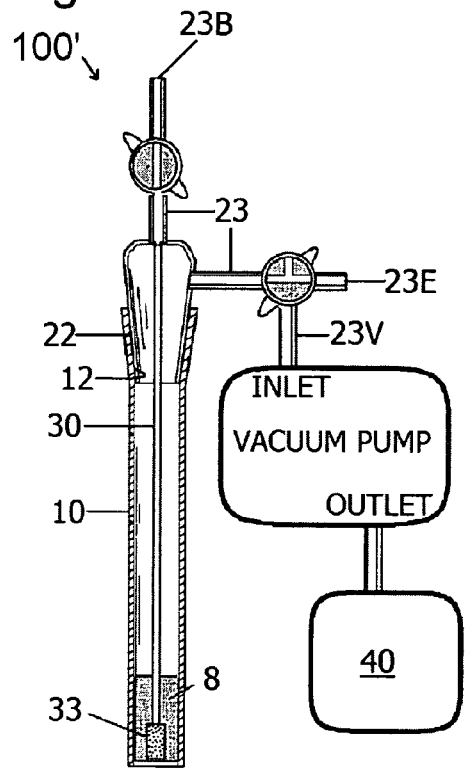
Fig. 15A
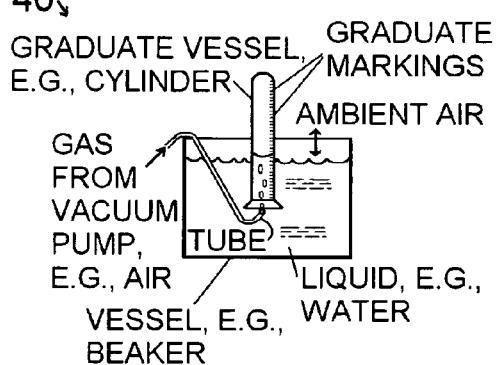
Fig. 15B
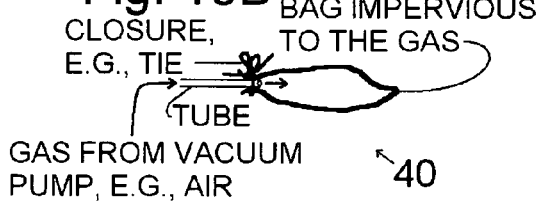
Fig. 15C
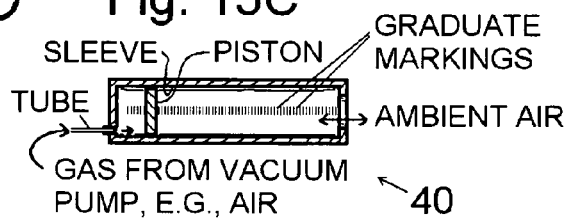
Fig. 16
PROVIDE TEST LIQUID 8, E.G., OIL, TO APPARATUS 100'
↓
ASCERTAIN VOLUME OF APPARATUS 100' WITHOUT AERATING THE TEST LIQUID 8
→ AERATE THE TEST LIQUID 8 WITH CHOSEN GAS, E.G., AIR
↓
ASCERTAIN ENTRAINED/DISSOLVED GAS PLUS VOLUME OF THE APPARATUS 100'
↓
DETERMINE VOLUME OF ENTRAINED/DISSOLVED GAS

TESTING FOR GAS IN LIQUID

This claims the benefits afforded under 35 USC 119(e) of provisional patent application Nos. 61/205,658 filed on Jan. 22, 2009 A.D., and 61/278,370 filed on Oct. 6, 2009 A.D. The complete specifications of those applications, to include, of course, their drawings, are incorporated herein by reference.

FIELD AND PURVIEW OF THE INVENTION

This concerns a method and apparatus for testing a liquid, for example, engine oil, for the presence of entrained and/or dissolved gas, for example, air. Foam production and decay and/or direct measurement of gas volume can be employed.

BACKGROUND TO THE INVENTION

The presence of air bubbles or foam in hydraulic fluids has virtually always been considered a negative condition because of the so-called "sponginess" shown by such liquids when applying hydraulic pressure to activate mechanical devices. See, e.g., Hodges, P., *Hydraulic Fluids*, John Wiley and Sons, 1996; Williams, L. "Aeration," GF-5 Video Archives (www.gf-5.com), 2008, Lubrizol, which relates to the same in automotive engines.

In engine oil, formation of foam in the operating engine by aeration is undesirable at hydrodynamically lubricated surfaces because it markedly increases potential for wear. See, e.g., Choi, J-K, et al., "Effect of Oil Aeration on the Minimum Oil Film Thickness and Reliability of Engine Bearings," SAE, Warrendale, Pa., Paper No. 932785, 1993; Nikolajsen, J. L., "Viscosity and Density Models for Aerated Oil in Fluid-Film Bearings," *Tribology Transactions*, Vol. 42(1), pp. 189-191, 1999; Chun, S. M., "A Parametric Study on Bubbly Lubrication of High-Speed Journal Bearings," *Tribology International*, Vol. 35, pp. 1-13, 2002; Jang, S., et al., "Study on the Effect of Aerated Lubricant on the Journal Traces in the Engine Bearing Clearance," *International Journal of Automotive Technology*, Vol. 6(4), p. 421, 2005.

Foam has been even more of a problem when recent engine designs have required engine oil to also function as a hydraulic fluid, particularly foam produced from release of any entrained air in the oil. See, Hodges, P., supra; Porot, P., et al., "A Numerical and Experimental Study of the Effect of Aeration of Oil in Valve Trains Equipped with Hydraulic Lash Adjuster," SAE, Warrendale, Pa., Paper No. 930997, 1993. These newer hydraulic functions such as cylinder deactivation and variable valve timing are more demanding of the engine oil than prior use of the oil to serve in such applications as in hydraulic valve lifters. Note, Hodges, P., supra.

As a consequence, a strong need has developed to distinguish among engine oils regarding resistance to the following:
1. Foam formation and foam retention in the crankcase;
2. Absorption of entrained air during engine operation; and
3. Liberation of entrained/dissolved gas when exposed to any relatively sudden decrease of pressure.

There are a number of engine operating conditions that can produce pressure decreases. For example, pressure drop is encountered by oil in the process of emerging from an oil gallery through which it has been pumped under the pressure required to overcome viscous resistance.

Thus far, according to a personal communication from 2009 with King, T., ILSAC/Oil Chairman, regarding past efforts to find an acceptable aeration test by the industries involved in the improvement of engine oil, this growing need to control foaming from entrained air has been said to be essentially unmet, and this is despite strong efforts on the part of the petroleum and additive industries. A testing exception is an older engine test, ASTM D 6894-08, "Evaluation of Aeration Resistance of Engine Oils in Direct Injected Turbocharged Automotive Diesel Engines," which, however, is expensive, imprecise, time consuming, and of limited availability.

Other art is known. See, Selby et al., U.S. Pat. No. 5,824,886 (Oct. 20, 1998), which discloses a foam tester; Hildebrandt et al., U.S. Pat. No. 6,009,748 (Jan. 4, 2000), which discloses a rapidly cyclable foam testing oven; ASTM D 892-06, "Standard Test Method for Foaming Characteristics of Lubricating Oils," and ASTM D 6082-06, "Standard Test Method for High Temperature Foaming Characteristics of Lubricating Oils." Compare, Selby, T., et al., "A New Approach to the Determination of Extracted Profoamants from Elastomeric Sealants," presented at the $12^{th}$ Esslingen Colloquium, Jan. 11-13, 2000, Esslingen, Germany.

Among drawbacks in such art is that a large, 26-pound sample must be employed to effectively run and obtain results from the engine aeration test. Sample size in the known bench foaming tests is required to be several hundred milliliters (mL) of sample. Also, the relationship among foaming, aeration, and gas entrainment is relatively unexplored but important to the use of lubricants for hydraulic fluid and/or engine oil applications.

It would be desirable, accordingly, to provide a simple bench test that can illuminate the foaming tendencies of air-entraining oil under a pressure drop, notably, for example, before the oil enters the field. It would be desirable to provide for greater accuracy and precision with such a test as well as to provide a bench test that is more revealing and perhaps predictive of future performance of an oleaginous liquid during and after use than that which is provided by the known art. It would be desirable to provide a bench test that would employ a smaller sample size than tests of the known art. It would be desirable to provide an alternative to the art.

A FULL DISCLOSURE OF THE INVENTION

Provided hereby is a method for testing a liquid, say, an oleaginous liquid or an ink, for instance, a lubricating oil, for example, an engine oil, for aeration, entrainment and/or dissolution of a gas and/or foaming, which comprises least one of the protocols of the incorporated domestic priority documents, in which the liquid is tested through generation of a foam, for example, through aeration with employment of a vacuum, which can be carried out at a controlled, elevated temperature, for example, about 150° C., and the foam measured as to volume generated; and further to those, a protocol in which a liquid as aforesaid is tested for an entrained/dissolved gas directly, say, by drawing off the entrained/dissolved gas with a high vacuum, which can be done following aeration that can be conducted under ambient pressure, for example, at a controlled temperature at or near ambient, say, at about 30° C. The gas can be air. One or more of the several protocols may be employed in conjunction with or as a check on the other(s).

Provided hereby as well is an apparatus for use in such testing, which comprises an outer, selectively sealable tube, which can be transparent, and which can serve as a vessel to contain a sample of a liquid as aforesaid to be tested; and, within the outer tube, a smaller generally vertical, inner tube also extending upward from and optionally out of the sealed outer tube. The smaller, inner tube is tipped at its bottom with an outlet capable of releasing a gas into the liquid sample, which may be released in a form of fine bubbles. The apparatus may be further provided with a contrivance for measuring contents of the sample within the outer tube and/or with a volume measuring device for ascertaining volume of released gas without generation of foam.

The invention is useful in testing of liquids, for example, engine oils.

Significantly, by the invention, the art is advanced in kind. One or more drawbacks or problems in the art are ameliorated if not overcome. Precision and accuracy in testing such liquids as inks, hydraulic fluids, and lubricating oils, including those for use in internal combustion engines, for the tendency of the liquid to develop foam, entrain gas, and release entrained and dissolved gas, are provided, in general, if not to a high degree, and testing methodology is made fast and simple, if not direct. The performance of the liquid can be revealed if not predicted for its employment in the field. Only a small sample is required. Significant and telling differences and similarities can be ascertained. For example, changes or differences in foaming tendency, aeration, and gas entrainment can be determined for fresh versus used motor oils. Repeatability is excellent. A viable, efficient alternative is provided.

Numerous further advantages attend the invention.

The drawings form part of the specification hereof. With respect to the drawings, which are not necessarily drawn to scale, the following is briefly noted:

FIG. 1 is a flow chart of a foam aeration testing method illustrating Protocols I and II.

FIG. 2 is a side plan view, with portions in section, of a foam aeration testing apparatus.

FIG. 3 is a side plan view, with portions in section, of another embodiment of a foam aeration testing apparatus.

FIG. 15 is a side plan view, with portions in section, of another embodiment of an apparatus hereof, one for direct measurement of volume of entrained/dissolved gas of a liquid.

FIGS. 15A, 15B and 15C are views of released gas volume measuring devices, which can be employed with the present apparatus, for instance, as of FIG. 15, to wit: an inverted, liquid-filled tube submersed in an open container of the same liquid (FIG. 15A); a flexible bag or balloon to hold released gas (FIG. 15B); and a sleeve and piston arrangement (FIG. 15C).

FIG. 16 is a flow chart of a released gas volume testing embodiment without attempting to generate foam, which illustrates Protocol B methodology.

The invention can be further understood by the detail set forth below, which may be read in view of the drawings. As with the foregoing, the following is to be taken in an illustrative and not necessarily limiting sense.

As mentioned previously, on one hand, a gas, for example, air, which may entrained and/or dissolved in a liquid, for example, an engine oil, can be ascertained with the generation and measurement of foam. Such testing can be carried out at an elevated temperature, for example, 150° C. The apparatus can be used to effect with the same.

According to such methodology, for the determination of foaming level, the outer tube can be unsealed and the inner tube positioned near the bottom of the outer tube. The assembly can be pressurized with the gas at a selected pressure, for example, ambient atmospheric pressure or slightly above, which creates a foaming condition that can be continued for a predetermined length of time in which the gas flows through the gas disperser at the lower end of the inner tube to form foam from the liquid and the gas escaping from the unsealed outer tube. After a certain predetermined time the flow of the pressurized gas can be shut off; the maximum foam height that is formed can be measured; and, if desired, the time for the foam to completely collapse can also be measured. Optionally, waiting for a predetermined time after such collapse—closing and sealing the inner tube and applying a pressure lower than atmospheric, i.e., a vacuum, to the fluid sample in the outer tube, may cause the gas entrained and/or dissolved within the test sample to form bubbles and leave the test sample liquid in the form of foam, which can be measured as an indication of entrained and/or dissolved gas in the test sample. Optionally again, the length of time between first applying the vacuum to the sample in the outer tube to when no further gas is liberated from the test sample can be measured as an indication of how tenaciously the test sample will retain the entrained and/or dissolved gas.

More specifically, pertinent apparatus 100 can comprise an elongate tube having a hollow interior to hold and, if desired, have monitored a liquid, for instance, an oleaginous liquid, therein, which has a sealable top portion for receiving a stopper under seal as well as, if desired, a monitoring assistance contrivance; and the stopper, which further has port(s) for entry of bubbling gas and drawing of vacuum; and an associated elongate, hollow wand in communication at a first position with the port for entry of bubbling gas, and, at a second position near or at a lower extremity of the wand, a plurality of fine gas-bubbling orifices.

Figure 4:
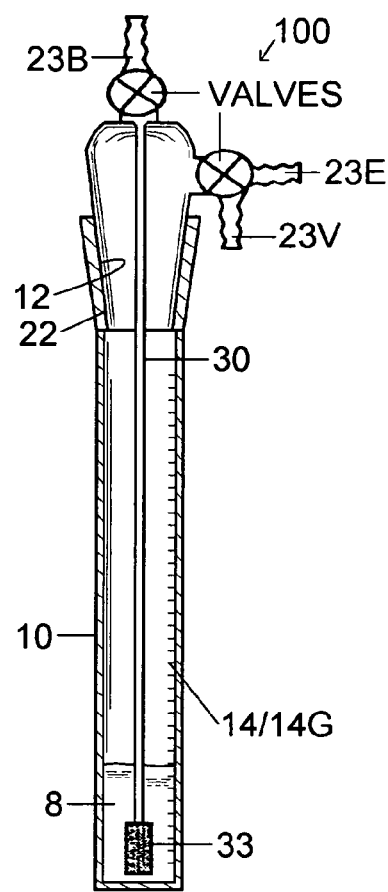
FIG. 4 is side plan view, with portions in section, of another embodiment of a foam aeration testing apparatus.

The apparatus 100 can be made of any suitable material(s), for example, substantially of glass, and is for testing liquid 8, say, for the making and collapsing of foam 9 under first and second pressures, for example, under ambient atmospheric pressure and then under a low pressure such as developed from a sink faucet aspirator or a vacuum pump. The apparatus 100 embraces elongate tube 10, which may have any suitable shape and size, for example, a cylinder, say with effective inside diameter 10 D of 0.7 inch (1.8 cm) and effective inside height 10 H of twelve inches (30 cm) for hollow interior 11, which contains the liquid 8 and foam 9. The tube 10 has sealable top portion 12, for example, a ground glass fitting, which may be provided with sealant 13, say, stopcock grease of petroleum and/or silicone; and can have monitoring assistance contrivance 14, for instance, etched and/or painted indicia in a form of graduate markings 14G for use with the naked eye, or a sensing instrument such as cooperating light 14L and sensor 14S for readout and/or manual or electronic input into a supporting computer. The tube 10 may have substantially flat bottom 15 for the purpose of providing a zero-height reference point for measuring the test liquid or foam height. Stopper 20, for example, of glass, has ground glass fitting 22 to fit into and cooperate with and take advantage of the sealable top potion 12 and the sealant 13 for sealing; gas port(s) 23, which can include port 23B for entry of gas for bubbling into the liquid 8 and possible formation of the foam 9, port 23E for exit of the gas left over during its introduction, and port 23V for drawing of vacuum or otherwise providing a low-pressure atmosphere to the interior 11 of the apparatus 100. The stopper 20 may include two- and/or three-way stopcocks, the moving and cooperating internal surfaces of which may employ the sealant 13 as well. Associated with the stopper 20 is elongate hollow wand 30, for example, of glass, say, with an outside diameter 30 D of 0.20 inch (0.51 cm), which is in communication at first position 21 with the port 23B so that the bubbling gas can travel therethrough, and which has, near or at lower extremity 32, a plurality of gas outlet orifices 33 such as provided by fritted glass, say, of 0.0008-cm diameter. In the apparatus 100 depicted in FIG. 2, the gas provided for foaming through the port 23B is shut off for the following step, if desired, of applying a vacuum through the port 23V. In the apparatus 100 depicted in FIG. 3, this action is accomplished by closing the upper stopcock and turning the lower stopcock so that it closes the air outlet 23B and opens the sample 8 to the vacuum source through the port 23V. Compare FIG. 4 (and FIG. 15).

Accordingly with the apparatus 100, among other things, especially with further respect to FIG. 1, the foam-building and/or foam-collapsing step(s) of the pertinent methodology may be repeated in succession as necessary or desired, for instance, to obtain a series of readings that, added together, may exceed the vertical capacity of the apparatus 100 to contain and/or indicate the presence of the foam from one foam-building step. In addition to pressure, time and/or temperature may vary within one test or be the same, and, overall, pressures, times and/or temperatures may vary from test to test, or be the same. A higher temperature may provide for more or less foam depending on the test liquid and any foam suppressants present. Any suitable gas or mixture of gasses may be employed.

On the other hand, the gas, again, for example, air, which may be entrained or dissolved in the liquid, again, for example, the engine oil, can be ascertained directly such as by drawing it out of the liquid by a vacuum and measuring it directly with the released gas volume measuring device subject to an ambient or other pressure, without an attempt to generate and measure foam. This can be conducted at or near an ambient temperature, for example, about 30° C.

The apparatus especially pertinent to the latter protocol may be the apparatus 100', which may be considered to be an apparatus, in general, as the apparatus 100 further provided with volume measuring device 40 for ascertaining volume of released gas without generation of foam. This can be considered to be "direct" measuring. Accordingly, as depicted in FIG. 15, in the apparatus 100', a monitoring assistance contrivance, for instance, etched and/or painted indicia in a form of graduate markings for use with the naked eye, to measure foam generation in the elongate tube 10, can be absent in comparison to the apparatus 100. Such a volume measuring device 40 can be an inverted clear glass or plastic tube filled with a liquid, for example, water, and having its open end submersed in a second upright vessel containing the same liquid that has an interface with air at ambient pressure, with the inverted tube having gradient lines on it to measure volume of the liquid in the inverted tube displaced by the gas, which can be introduced by a conduit, for example, a tube from the vacuum pump, which opens and enters the inverted tube near or just above its open end (FIG. 15A). Such a volume measuring device can comprise another contrivance, for example, a flexible bag or balloon that is impermeable to and filled with released gas drawn by the vacuum pump and perhaps passed through a conduit such as a tube from the vacuum pump so that the volume of released air trapped in the bag can be measured volumetrically, say, by direct measurement of its dimensions and/or by displacement of a liquid in a measuring container, or, say, by weight (FIG. 15B); a sleeve and piston combination for measurement of the position of the piston as a measure of volume of released gas provided to a space behind the piston in the sleeve (FIG. 15C); and so forth and the like.

Liquid sample sizes for the test protocols may be any suitable size, as may be desired or perhaps required by necessity, but the sample may be small, say, about from five to forty mL, to include about from ten to twenty-five or thirty mL. The sample may be about twenty mL.

As mentioned previously, any suitable gas may be employed. For example, the gas may be an inert gas such as helium, argon or nitrogen; a gas that, while somewhat inert, may have more of a propensity for reaction such as air, hydrogen, or oxygen; or a gas that perhaps may be even more reactive such as chlorine, hydrogen chloride, or sulfur dioxide. The gas may be air taken from the ambient atmosphere. The gas may be employed at ambient temperature, or it may be heated or cooled.

Accordingly, there may be included in the present methodology two general protocols, Protocol A and Protocol B. Protocol A includes as a distinctive feature or step attempts to generate and measure foam. Protocol A can be conducted at an elevated temperature. Protocol B includes as a distinctive feature or step the lack of an attempt to generate and measure foam; rather any entrained/dissolved gas is attempted to be measured directly as it were, without relying on foam. Protocol B can be conducted at a moderate temperature. The Protocol A and Protocol B test methods can be employed to augment data from and/or check on one another. In other words, a particular sample may be conducted through a Protocol A test method and through a Protocol B test method.

SOME DEFINITIONS AND DISTINCTIONS

Unless otherwise noted, the following definitions and distinctions apply herein, to include with Protocol A and Protocol B testing as would be appropriate:

AERATION—Introduction of relatively finely divided gas into a liquid. Example: foaming tests of lubricating oil such as ASTM D892 or D6082.

DISSOLVED GAS—Gas that is just sufficient to occupy all the natural interstices of the freely moving molecules composing the liquid together with any contaminants.

ENTRAINED GAS—Gas that, at constant pressure and temperature, is capable of increasing the gas content of a liquid up to the point of saturation, i.e., short of forming visible bubbles within or on top of the liquid.

FOAMING—Foam formation above a liquid by:
1. Aerating the liquid, or
2. Release of entrained/dissolved gas within a liquid under some decrease in pressure on the liquid.

FOAM LEVEL—The maximum height to which foam rises or is permitted to rise.

FOAM RISE TIME—The time required for the foam to reach the foam level as described immediately above.

FOAM FILL RATE—The rate at which the previously defined foam level is reached.

COLLAPSE TIME—The length of time required for the foam formation in these tests to collapse to the point of showing some portion of the liquid surface.

COLLAPSE RATE—The overall rate at which the foam collapses.

Instrumental Apparatus in Protocol a Testing

The instrument 100 was designed to be simple to operate. Small sample size was also considered a benefit in increasing the number of samples able to be taken for test under engine operating conditions. The sample size selected was 20 mL.

As one aspect hereof, it was desired to determine if the ability of a given engine oil to release entrained gas was related to its ability to absorb gas. Accordingly, the present protocols of Protocol A (Protocols A1 and A2) included effort to saturate the lubricant with gas (here, air) as the ability to determine how readily the engine oil would release any thus entrained/dissolved gas when pressure was reduced. For this, the instrument 100 can subject the oil 8 to any level of vacuum desired. All work employed a portable laboratory vacuum pump and its maximum vacuum was applied to a stopcock effectively metering the rate of vacuum application.

The instrument 100 was constructed of glass. A thin inner glass tube 30 reached from the gas inlet at the top of the apparatus down to a fritted-glass, air-dispenser 33 of the fine porosity (approximately 0.008 mm average pore size, 24-μm porosity and 470 mL/min permeability, with the "porosity" and "permeability" as defined in ASTM D 892-06). The top of the fritted-glass air-dispenser 33 was designed to be well below the surface of the 20-mL oil sample 8 to assure sufficient liquid for formation of foam 9. The outer precision glass tubing 10 of the apparatus 100 carried graduated marking 14G to measure foam volume.

Figure 5:
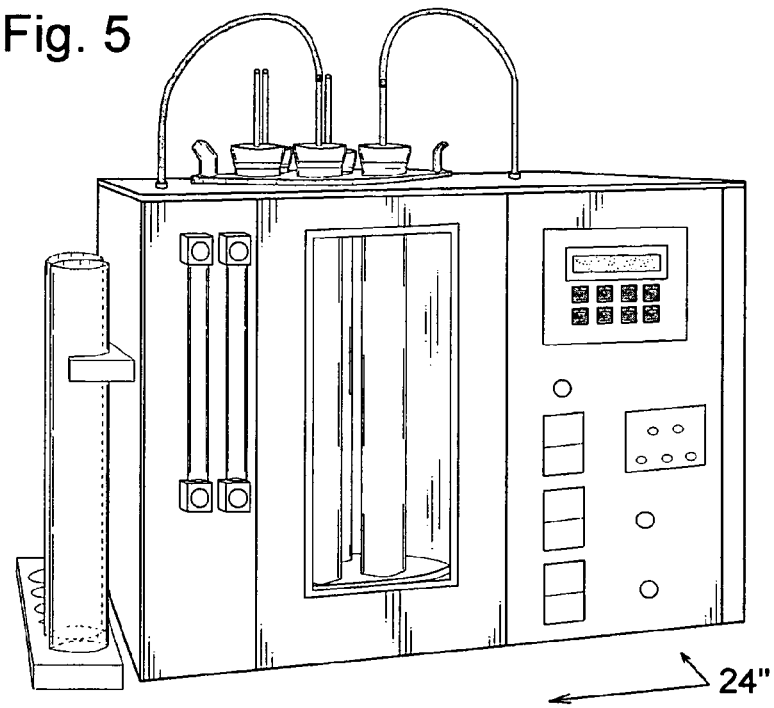
FIG. 5 is a front view of an air bath for controlling temperature.

Temperature of the oil and air was considered likely to be an important factor herein, and the present work under Protocols A1 and A2, each a variation of Protocol A, was done at a closely-controlled temperature of 150±0.5° C. in an air-bath shown in FIG. 5, which is designed for ASTM foam tests. Note, the Tannas Foam Air Bath TFAB) laboratory instrument available from Tannas Co., Midland, Mich. (www.tannasco.com). Compare, U.S. Pat. Nos. 5,824,886 and 6,009,748. The rate of gas supplied to the instrument 100 was controlled by either of two flow-meters on the left front of the air-bath, and foam height and collapse time were viewed through the insulated front window shown.

Immediately after the initial aeration/saturation (foaming) step and in the subsequent vacuum test cycles, all foam rise and collapse times were measured by stopwatch.

Test Protocols for Protocol a Testing

The following test protocols were employed:

General Preparatory Conditions

The air bath into which the instrument 100 was inserted was preheated to 150±0.5° C. When the air bath was at temperature, the instrument 100 containing 20 mL of the test oil was placed in the bath carousel visible in FIG. 5 and allowed to come to the bath temperature.

One of the two gas flowmeters on the upper left face of the TFAB instrument (FIG. 5) was connected to the gas inlet 23B (FIG. 4), the gas inlet valve then closed, and the gas outlet valve opened to accommodate gas expansion when heated.

After placement of the instrument 100 in the air bath, the sample temperature was measured. Above 20-25 minutes later, when the sample was 150° C., the gas inlet valve on the instrument 100 was opened and the valve on the air bath gas flowmeter adjusted to provide air at 20 mL/minute flow rate to the fritted-glass air diffuser 33 thus causing the oil sample 8 to foam.

Protocol A1 used in a first study

During a period of 10±0.1 minutes of aeration, the final foam level reached was recorded. After the aeration period, the air inlet valve on the instrument 100 was closed, and the foam caused by aeration allowed to collapse. Collapse time to a visible liquid patch on the surface of the sample was measured by stopwatch.

Exactly 5.0±0.1 minutes after the foam had collapsed, the vacuum available from the portable vacuum pump through a metering stopcock was applied at which point the air-saturated sample began to release air in the form of foam. The amount of foam that could be generated by the entrained air at this vacuum was greater (at least for the oil samples tested in these studies) than the capacity of the instrument 100. Accordingly, the amount of foam was measured in a series of steps in which:
1. Foam was allowed to reach a variable but recorded level in the graduated outer glass tubing;
2. The vacuum was then immediately closed off;
3. When the foam had collapsed, the vacuum was re-imposed on the oil to produce more foam;
4. Cycle step Nos. 1-3 above were repeated until no more foam was produced at which point the test was ended and the foam levels summed to obtain total volume values.

Protocol A2 Used in a Second Study

Observations made during the application of Protocol A1 led to refinement in gathering information in the application of the present sub-protocol, Protocol A2.

First of all, the initial foaming period was shortened from 10.0±0.1 minutes since it was evident that final foam level was reached within a minute or slightly more for these test oils at 150° C. However, the 5-minute pause between foam collapse and the first application of low vacuum was not changed.

Applying more delineation, after saturating the oil with air and obtaining foam height and collapse time, the series of vacuum application steps were made more precise to gather further data. These steps were:
1. Foam was allowed to reach the 50-mL mark in the graduated outer glass tubing;
2. Time for the foam to rise to this volume was timed and recorded;
3. Vacuum was then quickly closed off;
4. Time required for foam collapse was recorded;
5. Vacuum was immediately re-imposed on the oil to produce more foam;
6. Cycle step Nos. 1-5 were repeated until no more foam was produced at which point the test was ended, and
   a) individual and summed foam levels were recorded;
   b) individual foaming times to the 50-mL mark were recorded, and c) individual foam collapse times were recorded.

At this point all of the entrained/dissolved foam values on the tested oil were summed, tabulated and compared, as were the foam rise and collapse times and rates.

Test Oils

PROTOCOL A1—Two oils were obtained for a first set of examples. These two oils were used by the inventor's laboratory as reference oils for ASTM foaming tests. Oil F-100 was a somewhat lower-foaming base oil consistently giving a total foam height, i.e., foam plus liquid height, of 220-225 mL and essentially zero foam collapse time at the temperature of 150° C. in ASTM Test Method D6082. The second, Oil F-200, was formulated SAE 10W-30 engine oil with higher foaming tendency, a total foam height of 290-300 mL and 17-19 seconds foam collapse time. The latter oil was tested twice here to obtain some indication of test repeatability.

PROTOCOL A2—In a second set of examples, two samples of engine oil, one fresh oil (Oil N) and the other the same oil after a 300-hour engine dynamometer test (Oil UN), were employed as kindly made available by J. Linden of General Motors Fuels and Lubricants Dept. Reference Foaming Oil F-200 was also run in Protocol A2 for comparison to Protocol A1 results.

In this series of tests, the fresh Oil N was run once through Protocol A2 (Test A). However, the used engine oil, Oil UN, was run three times in the following series:
1. TEST B: Protocol A2;
2. Test B': the sample from Test B was re-run under the full Protocol A2 while still in the instrument 100;
3. Test B": a second fresh sample of the used oil was tested (as in Test B) under the Protocol A2 to determine a measure of repeatability.

Results and Observations Concerning the Study Using Protocol A1

Figure 6:
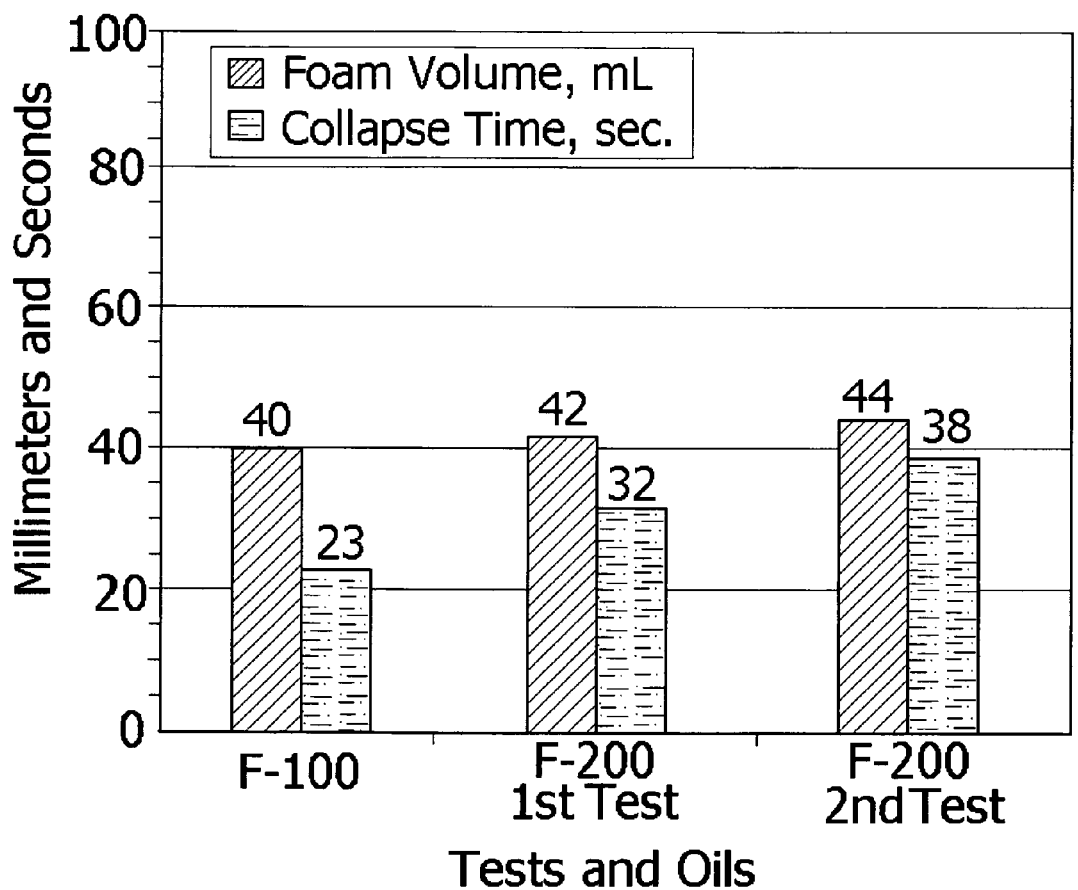
FIG. 6 is a graph of aeration (foaming) results with Protocol A1.

FIG. 6 shows the results of the aeration or foaming portion of the study of Oils F-100 and F-200. The Y-axis is labeled in units that represent both milliliters of foam and seconds for the time to complete foam collapse. Although the purpose of this step in Protocol A1 was to try to saturate the oil with air, this additional information was thought useful and gathered as well.

As mentioned, Oil F-200 was run twice to test repeatability. Regarding difference in foam height, no substantial difference is shown between F-100 and F-200 in FIG. 6 although there is meaningful difference in foam collapse time. Repeatability of the two runs on F-200 is reasonable for a new protocol and instrument. (The present technique might also be suitable for use in obtaining foaming tendency data.)

The first step of Protocol A1 was an effort to saturate the oils with air. Following this step, the primary purpose of Protocol A1 was to see how much air could be drawn from these presumably saturated oils by measuring the air released as foam under metered full vacuum.

Figure 7:
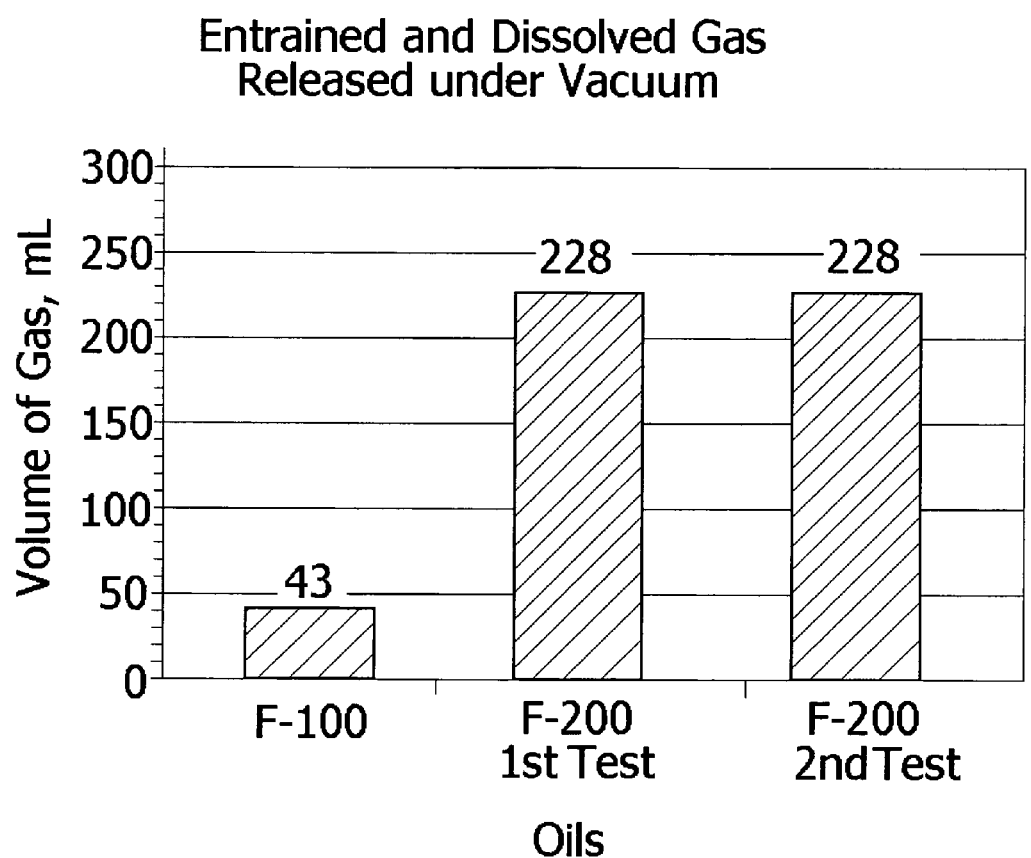
FIG. 7 is a graph of volume of entrained air released.

FIG. 7 shows the volume of air-filled foam generated by releasing entrained air under such vacuum.

The major difference between the foam volumes of Oil F-100 and Oil F-200 were surprising when compared to little or no difference exhibited in the simple foaming tests shown in FIG. 6. Moreover, repeatability of F-200 shown in FIG. 7 was also gratifying. These data implied that there are substantial and repeatable differences in the air-entrainment capacity of oils. This implication led to thought concerning the nature of the relationship between the molecular composition of liquids, their additive content, and the manner in which gases are entrained.

Comparison of the data of FIGS. 6 and 7 also suggested that a foaming test such as ASTM D6082, in which oil is simply aerated with externally provided air and the foam volume measured, may not provide the kind of information needed to compare the tendency of oils to release entrained/ dissolved gas. Specifically stated, considering the sources of gases producing the data of FIG. 6 compared to FIG. 7, the foams rise from entirely different sources—one from an extrinsic gas source essentially unrelated to the oil and the other an intrinsic source directly rising from and related to the nature of the oil's capacity to absorb air.

Results and Observations Concerning the Study Using Protocol A2

As previously noted, information gained from Protocol A1 was helpful in designing Protocol A2 which, as will be shown, was considerably more informative.

In this study using the second protocol, the test oils and tests were:
1. The two automotive engine oils, Oils N and UN, which were compared in Test A (Oil) and Test B (Oil UN);
2. A full re-test of Oil UN from Test B (identified in the following graphs as Test B') without removing it from the instrument 100;
3. A replicate test on a second, fresh sample of Oil UN (identified as Test B"); and
4. An analysis of F-200 (Test F-200) from Protocol A1 to serve as "bridge" data comparing results of Protocol A2 to Protocol A1 and to also compare the two fresh engine oils, Oils N and F-200.

Figure 8:
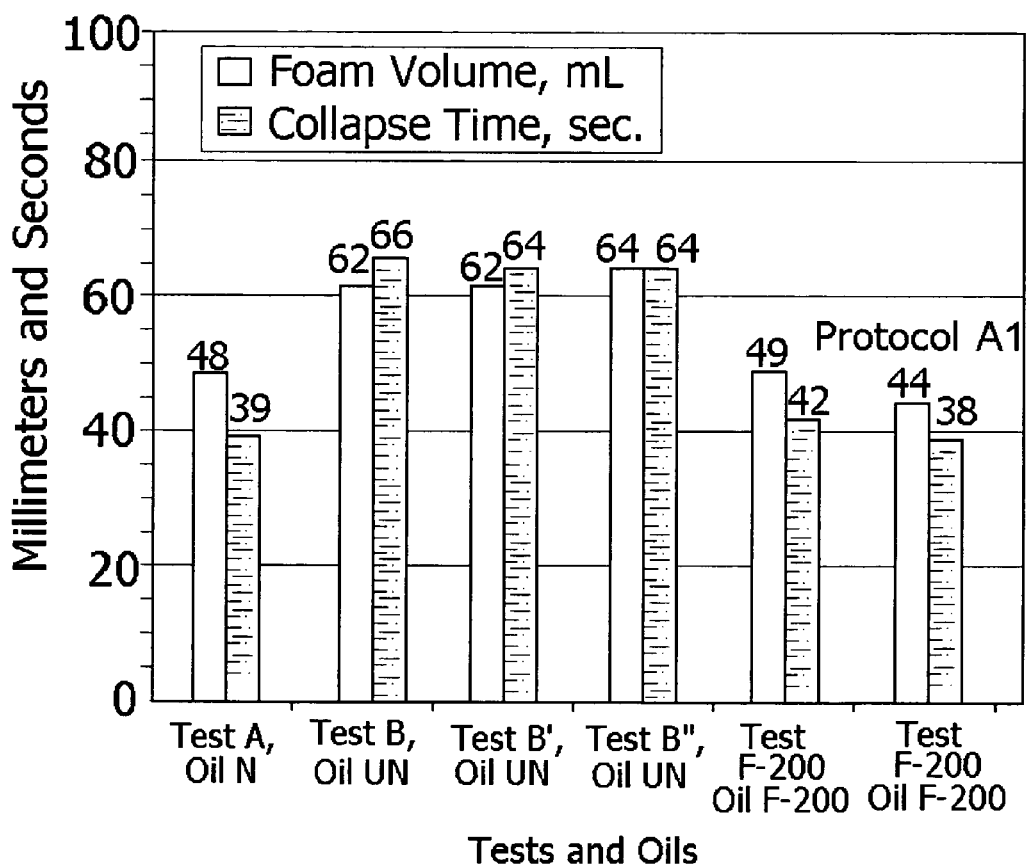
FIG. 8 is a graph of total foam volume and foam collapse time during aeration at atmospheric pressure.

FOAM RESULTS FROM AERATION/SATURATION— FIG. 8 shows the resulting total foam and foam collapse time obtained from aeration of the three oils. It is evident that, while there is a clear difference between fresh Oil N in Test A and the corresponding Oil UN in Tests B, B' and B" in susceptibility to foaming and foam collapse time, all three runs on the latter oil, B, B', and B" are closely comparable. Also of interest, fresh engine Oils N and F-200 gave very similar results. Further, foam level and foam collapse time results on Oil F-200 are reasonably similar in results to those of Protocol A1 (also shown to the right in FIG. 8 bars).

AIR VOLUME RELEASED—The next series of steps in Protocol A2 was to measure the response of the oils in the five tests regarding the manner of release of entrained and dissolved air by the:
1. Volume of air released as foam from the test oils under metered full vacuum;
2. Time required for the foam to rise to the permitted limit of 50 mL, and
3. Time required for the foam to collapse after the vacuum was closed off.

Figure 9:
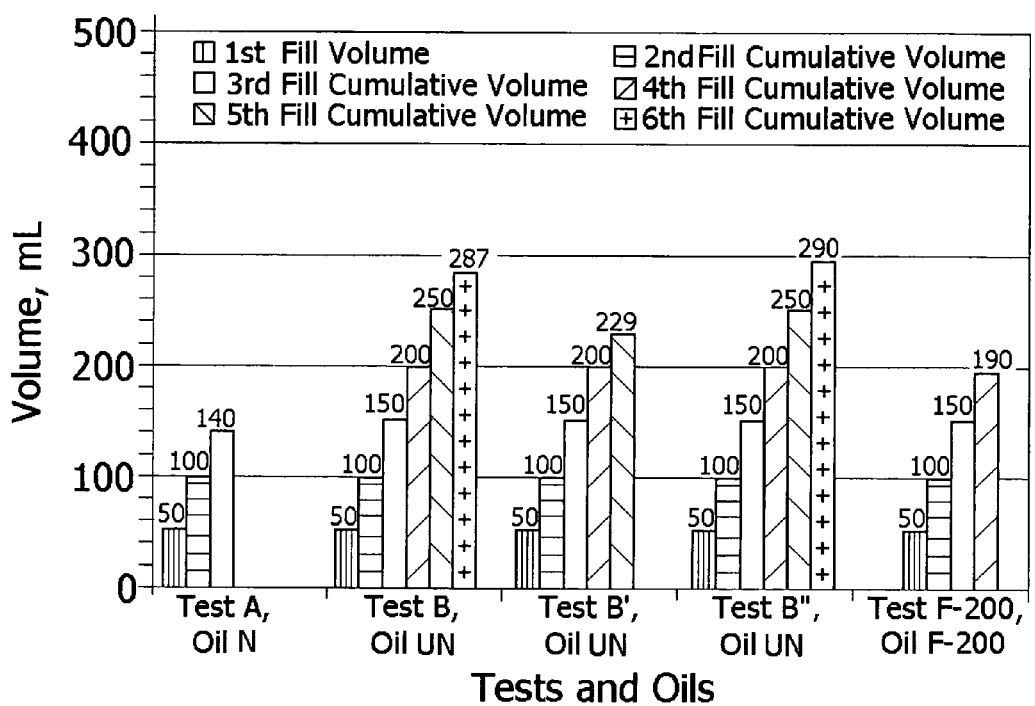
FIG. 9 is a graph of progressively summed foam values released from entrained and dissolved air in vacuum tests.

The first analysis was of the volume of air released as foam from the test oils, and such is shown FIG. 9, which is revealing. Since the total volume of entrained and dissolved air in the oils is released in a series of 50-mL steps until the last step where the available air is exhausted, the value in mL above each bar represents the sum of the foam volume for that particular oil is that point of test and the last value in each set represents the total volume of the foamed air released during the test under the same metered high vacuum (when no more foamed air can be extracted from the oil at this vacuum).

Figure 10:
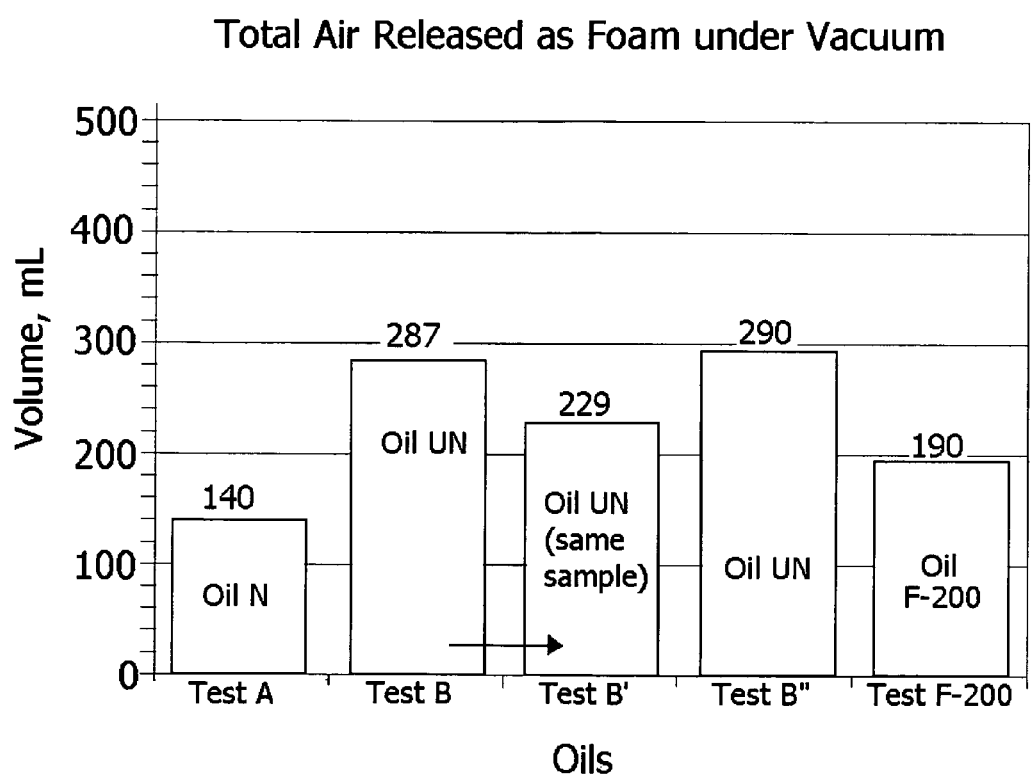
FIG. 10 is a graph of volume of foam generated from Protocol A2 tests.

For ease of comparing results on the fresh and used samples of the engine oil, FIG. 10 presents the final foam volumes shown in FIG. 9 on the engine oil tests.

It is evident that comparing Oil N with Oil UN:
1. The entrained air released as foam from saturated fresh Oil N in Test A is repeatably increased by about 100% when Oil UN is analyzed in Tests B and B", and
2. Reduction in entrained air foam volume was shown by re-analysis of one sample of Oil UN (Test B').

Comparing the formulated engine oils Oil N and Oil F-200:

3. Considerable difference was shown in regard to foam volume (140 Ml for Oil N versus 190 mL for F-200) even though their aeration foam levels were the same (see FIG. 5).

From the foregoing information, it seems apparent that:
A. Extended engine oil exposure to the operating engine had increased the oil's capacity to capture, contain, and release air under the test protocol applied.
B. Clearly there are factors in engine oil formulation that affect their air-entraining capacities.

The repeatability shown in replicate Tests B and B" was again surprising. In comparison, Test B' (which was very similar to Tests B and B" in initial aeration—noting FIG. 8)—a second test (Test B') on the very same sample of used oil from Test B) performed without removing the oil of Test B from the instrument 100—released a smaller volume of foamed air (only 229 mL in Test B' versus 287 and 290 mL in fully replicate Tests B and B", respectively).

This response suggested (in pertinent comments made by J. Linden and/or the inventor in discussing the potential significance of the data collected and presented by the inventor to a small group in Warren, Mich. in February of 2009 A.D.) that some of the components of Oil UN were removed in Test B during the application of Protocol A2. Perhaps these were in the form of volatile components such as fuel or other blow-by products absorbed by the engine oil during its exposure to engine operation or by high volatility oil components.

This result raises the question of what various forms of gas-producing components of used oil contribute to entrained foam and release.

FOAM FILL TIME—In preparing for the gathering of data concerning total foam volume produced by the fresh and used engine oil in Protocol A2, an interesting question was whether the release of entrained and dissolved air became either more or less constrained in its release by the oil under the low vacuum conditions applied. This is shown in FIG. 11, where time for the foam to rise to the 50-mL mark was also measured.

Several observations can be made. All the data were consistent in finding that air was released in all tests with greater and greater difficulty as the cycles continue.

Figure 11:
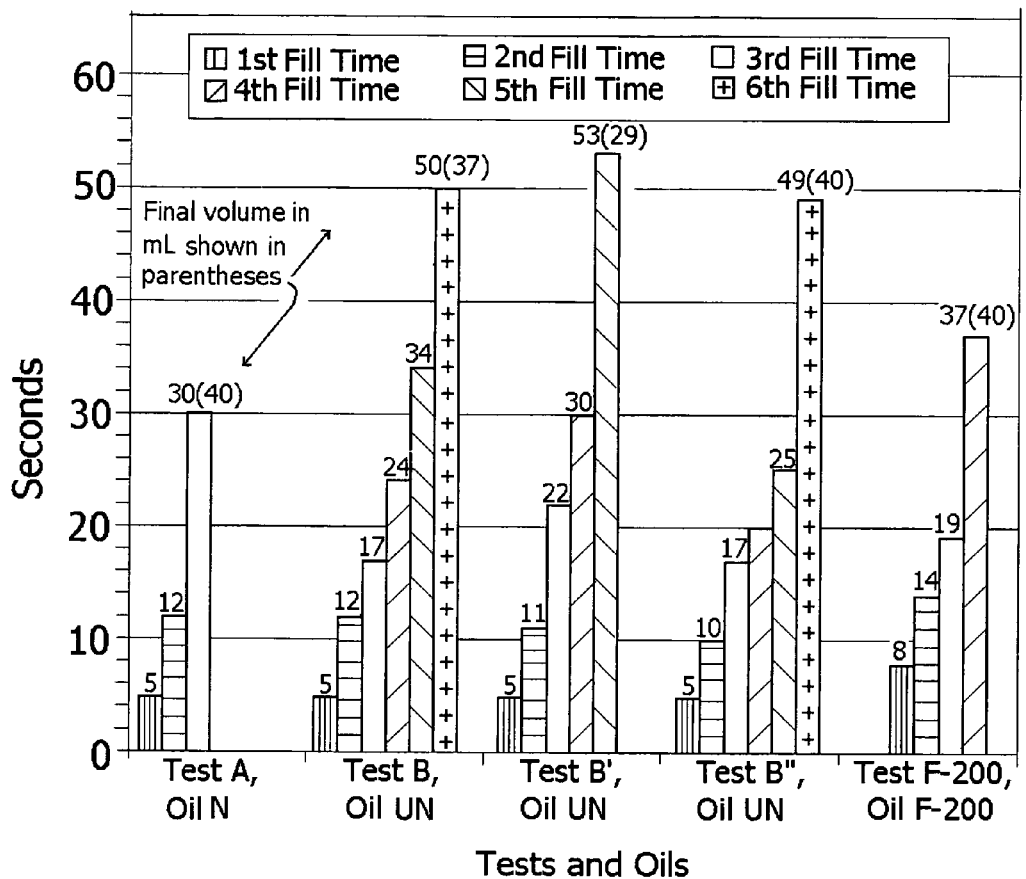
FIG. 11 is a graph of sequential foam formation.

Interestingly, FIG. 11 indicates that the last volume of air to be released (comparing the Test B, 24; Test B', 30; Test B", 25; Test F-200, 37(40)) is slowest in each test despite the fact that this last remnant of air in the fluid did not produce enough foam to reach the 50-mL mark. This raises some interesting considerations about what this last volume of air represents regarding oil solubility.

Once again, the two replicate Tests B and B" were very similar and indicated the repeatability of this portion of Protocol A2. In comparison, Test B' (the second full test on Oil UN from Test B) showed the slowest foam fill times from the third cycle on.

Figure 12:
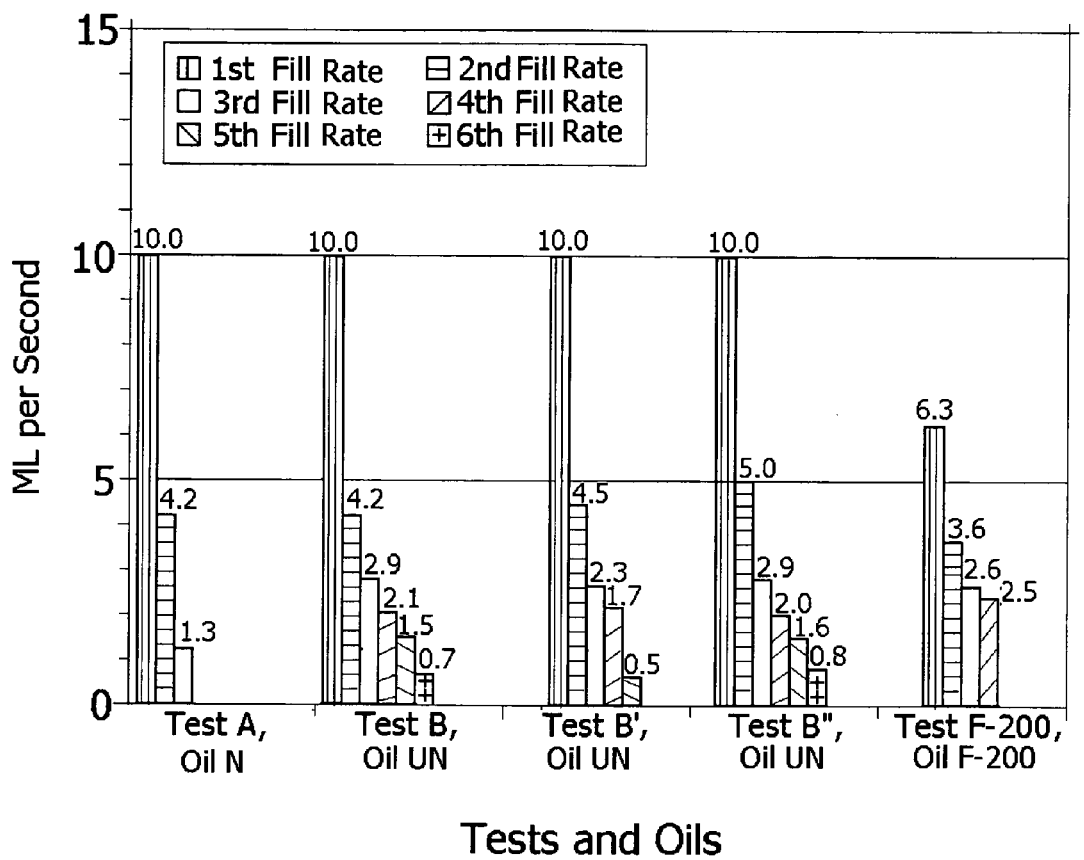
FIG. 12 is a graph of rate of sequential foam formation.

FOAM FILL RATE—To obtain a different perspective of the previous data on foam fill time and the increasingly slow fill response observed (particularly on the last cycle), the data were re-calculated to yield rate of foam formation. This is shown in FIG. 12.

Two observations that stand out in this view of foam rising rates are:
1. Differences in the initial and sequential rates of the fresh reference engine oil, F-200, compared to the fresh engine oil, Oil N, Test A, and
2. Tests of B and B", which again show good repeatability.

The first observation again leads to the question of the role of oil formulation and composition in absorbing and retaining air or other gases. It certainly suggests tests of all forms of base oils with their different molecular configurations that may reveal more about how gas is absorbed and retained.

Figure 13:
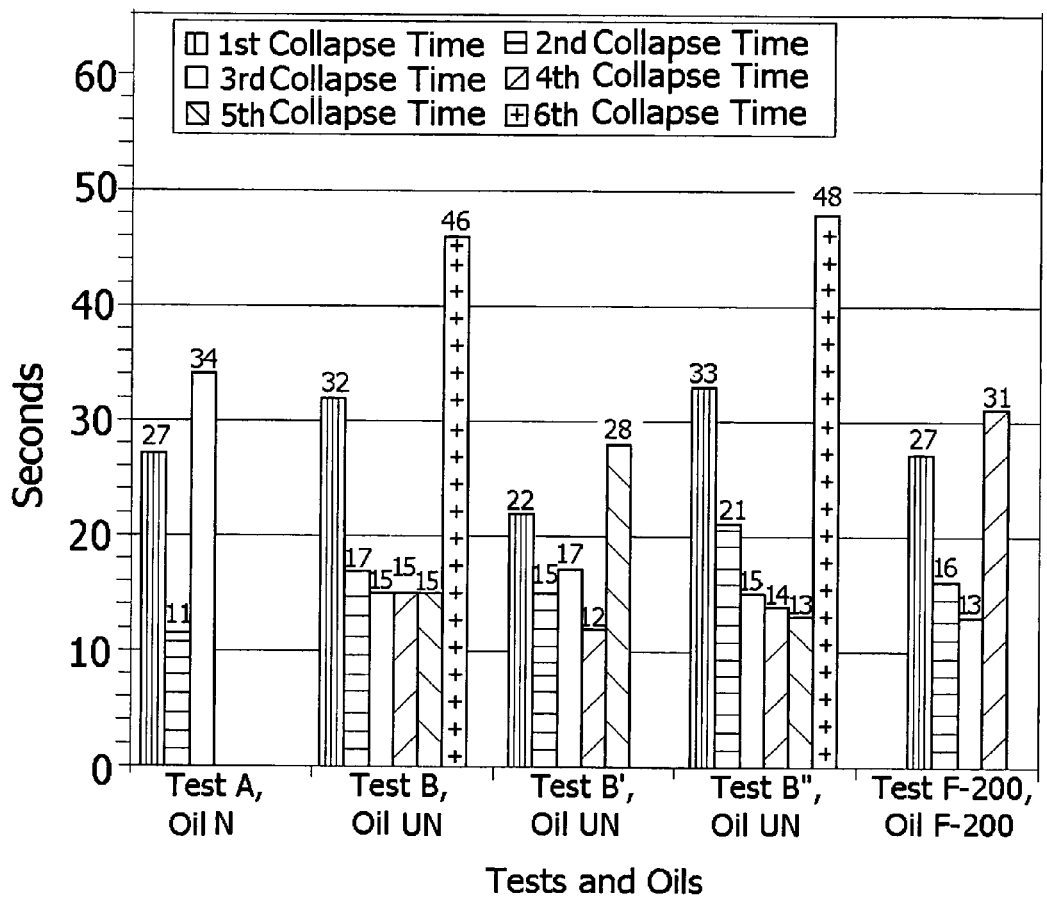
FIG. 13 is a graph of collapse time of sequential foam formation.

FOAM COLLAPSE TIME—After the formation of foam in the sequential series shown in FIG. 11, the collapse time for the foam formed under vacuum was measured. Results are shown in FIG. 13.

It can be observed that, up to the final step, the collapse time either diminished or stayed relatively constant. However, in every test, the final collapse time was markedly extended beyond any previous value for each oil tested.

It was also observed that Tests B and B" were again closely similar in results.

FOAM COLLAPSE RATE—For the same reasons presented previously for determining the rate of development of foam, the rate of foam collapse was also calculated to find if any other relationship were revealed. This is shown in FIG. 14 for the five tests.

Figure 14:
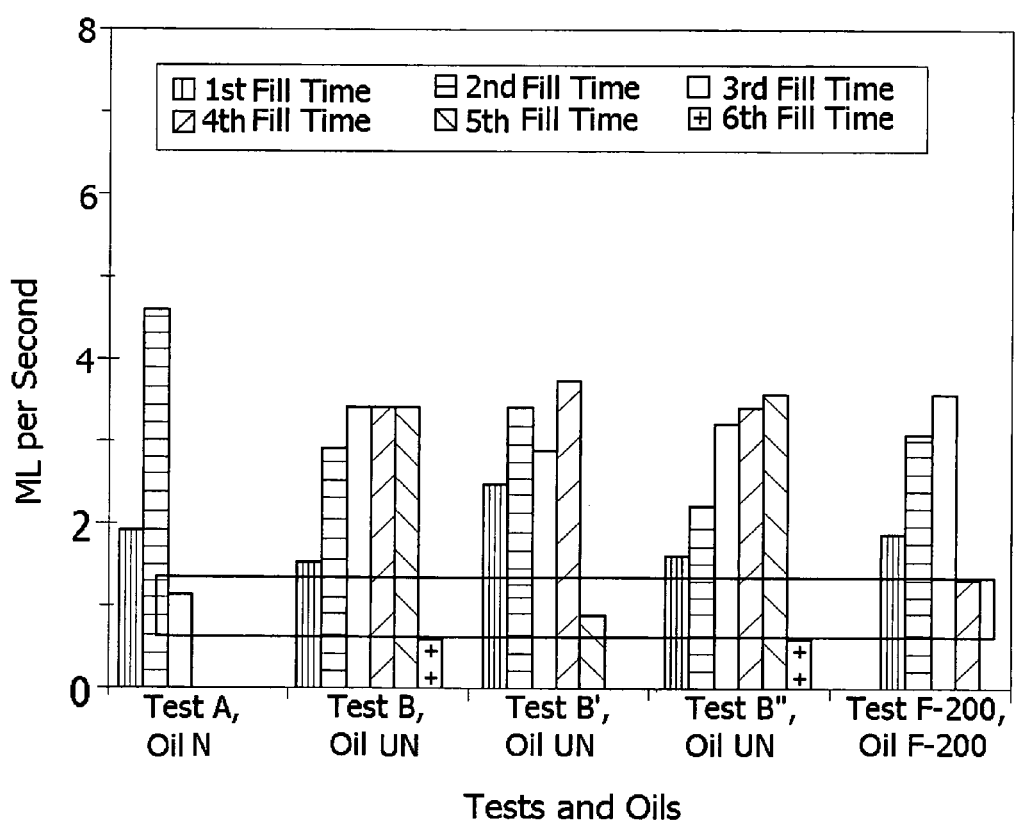
FIG. 14 is a graph of collapse rate of sequential foam formation.

In appraising the data and, in particular, the rate of collapse of the final volume for east test, these final rates collapse are all fairly similar as shown by the horizontal band in FIG. 14 indicating the level of similarity in all five tests. This similarity may indicate a similar mechanism operating in the removal of the final amount of entrained air.

Discussion Based on the Protocol A1 and A2 Tests

OBSERVATIONS—In these studies, it is evident that there can be significant differences between foamed air released from fresh engine oil and its used oil counterpart. Moreover, these differences are surprisingly repeatable as shown by the data obtained on the used engine oil. It remains to be determined whether and to what degree this difference would be found with other engine oils—formulated with different base oils and additives—at different temperatures and viscosity levels. However, comparison of two fresh engine oils shows that formulation differences can have meaningful effects.

It is likely that the instrument 100, with the varied protocols that can be used with it, should be able to repeatedly measure effects of both oil formulation and response of engine oils to engine operation.

As well, it has been indicated that typical foaming tests at atmospheric pressure such as ASTM D6082 may not be of significant technical value regarding the effects of air entrainment. It is even possible that such aeration-based atmospheric foaming tests may be negatively related to the foam produced from entrained air released under lower pressure since the processes of aeration foaming versus foaming from entrained air release are entirely different mechanisms.

These Protocol A1 and A2 tests were performed under limited conditions of higher temperature and its related effects on viscosity and other temperature-dependent properties. Similar studies conducted at different temperature would be very interesting to perform considering the expected difference in Brownian motion of the oil molecules and the formation and frequency of availability of interstices.

The different responses of a given oil in the sequential test protocols in both foam rise and foam collapse times also suggests that these factors may be important to the choice of engine oils and change with their composition and the factors associated with the temperature of study.

BASIC CONSIDERATIONS—From the viewpoint of the fundamental nature of how a gas is absorbed into a liquid, the instrument 100, its supporting air bath, and the opportunity of developing a number of relevant protocols may lead to more basic studies of the molecular configurations of liquids and their dissolved and/or entrained gases.

Taking a somewhat simplistic view and considering only physical interactions, the absorption of a gas into a liquid may be viewed as a mutual molecular accommodation or as a displacement phenomenon in which the gas fits reasonably well into the interstices generated by the shape and motion of the liquid. Of course, oil additives may be expected to have a modifying effect on the macromolecular relationships of gas-entraining oil.

Perhaps, properly applied, the approach presented herein may reveal more about the role of surface tension at both molecular and macromolecular levels in oils and other liquids.

Although experiments that would have more clearly defined the relationship have not yet been performed, the inventor has, in past unreported work on hydraulic fluid, observed that when virtually all remnants of air in a fresh hydraulic fluid have been removed by the imposition of zero absolute pressure, even though exposed to ambient air conditions, the fluid remains relatively free of air content for some period of time afterward. This was viewed as implying that removal of air from the hydraulic fluid did not create an energy-satisfying "hunger" for restoring minimum air content—rather the contrary. Thus, this response might indicate that a different molecular interrelationship forms among the liquid molecules in the absence of gas thus reducing the size and/or frequency of interstitial voids and creating a different relationship among the liquid molecules that is, to some degree, resistant to the intrusion of gas molecules. Some of the data in the present examples (noting FIGS. 13 and 14, and their discussion) tend to support this view in accounting for the markedly slower collapse time of the foam containing the final air removed from test oil under vacuum. From this viewpoint, the first stage of gas presence in the liquid might be the stage in which the gas is distributed about the primary liquid interstices until they are filled. Once might visualize this as the "just-soluble" accommodation level of gas in liquid. From this level, further entry of gas into the liquid might take the form of air entrainment in which a large quantity of gas might be accommodated by the liquid in conjunction with the "just-soluble" gas, which has lodged in and opened the oil interstices making them available for entry of more gas. Finally, a stage would be reached where no further gas could be retained without violating the basic nature of liquid contiguity.

All of the foregoing conjecture, if so, could lead to a better understanding of the large role of those molecules affecting surface tension and gas entrainment of a liquid at a macromolecular level.

Epilogue Based on Protocols A1 and A2

This disclosure presents an initial study of the behavior of air-saturated fresh and used engine oil and mineral base oils at 150° C. in tests conducted in the specially designed instrument 100 using two test protocols under the Protocol A. Both of these protocols (A1 and A2) applied metered high vacuum after presumed air saturation of the test oils to determine the amount of air released as foam from the test oils. Results showed that:
1. The data produced by both test protocols were surprisingly repeatable compared to other atmospheric-pressure, aerating, foaming tests such as ASTM D6082 and ASTM D892.
2. A marked increase of entrained air foam content was shown when extensively used engine oil was contrasted to its fresh counterpart.
3. Some of the results suggested that simple foaming tests of oil at atmospheric pressure may not produce values significant to the hydraulic application of engine oil.
4. The protocols with the instrument 100 differentiated among two fresh engine oils regarding their ability to release entrained air.
5. The protocols with the instrument 100 also clearly differentiated among a new and used sample of the same engine oil and also showed that components gathered or formed in the used oil during engine use also affect air release from engine oil.
6. Variation of temperature, levels of pressure decrease (vacuum), viscosity, choices and mixtures of gases, surface tension, and combinations of these variables offer a number of potential protocols which may illuminate other relationships between oils and gases.
7. This approach may also determine the effect of choice of additives and base oils on engine oils regarding their hydraulic functionality. In addition, it may be possible to develop additives that interfere with either the absorption of, or release of, entrained gas (over and above their effects on surface tension and the size of bubbles when released).
8. On a more basic level, these examples suggested that approaches utilizing the variations of the principles applied herein could be useful in developing a more fundamental understanding of the liquid and gas states and their interrelationship at the molecular level.

Modern engines rely more and more on the engine oil to serve increasingly complex hydraulic functions such as, for example, controlling cylinder deactivation—a way or means of significantly increasing fuel efficiency. However, the success of hydraulic methods of activating mechanical responses in engines (or other mechanical devices) is dependent on the degree of incompressibility of the hydraulic fluid. As a consequence, those engine oil properties that impart susceptibility to foam formation in areas of hydraulic operations of the engine are detrimental to the engine's performance and durability.

These examples represent an initial study of aeration, air entrainment, and air release under pressure decrease using a simple bench test. The preliminary information reported suggests the potential application of the instrumental approach developed to measure the rate of foam formation from the air entrained in engine oils and the resistance of such foam to collapse.

From a broader viewpoint, these examples provide a relatively precise means of viewing the molecular dynamics of gas in lubricants and other liquids.

Instrumental Apparatus in Protocol B Testing

The instrument 100' also was designed to be simple to operate. It was in essence the aforementioned instrument 100 but connected past the vacuum pump output to a volume measuring device 40. The instrument 100' has a leak-sealed system. Note, FIG. 15. An air over water measuring device employing an inverted graduated cylinder was employed. Compare, FIG. 15A. Small sample size was also considered a benefit in increasing the number of samples able to be taken for test under engine operating conditions. The sample size selected was 20 mL.

Rationale of Protocol B Testing

Protocol B testing represents a method of directly measuring the volume of entrained and/or dissolved gas released by an aerated liquid. In comparison to Protocol A testing, the reason for this approach was to:
   A. Obtain a direct rather than an indirect measure of the gas volume;
   B. Ameliorate if not eliminate the gas-volume expanding effects of sample temperature and vacuum imposed in Protocol A testing; and
   C. Eliminate the apparent boiling of the liquid, for example, oil, under high vacuum and high temperature.

Protocol B Used in Another Study

In general, the Protocol B testing of this example included the following steps:
   1. Install the test oil 8 in the instrument 100'.
   2. Obtain the volume of the instrument 100' without aerating the sample 8 by drawing off the air in the instrument 100' under high vacuum with the vacuum pump and measuring it with the volume measuring device 40.
   3. Aerate the sample 8 with the gas chosen, for example, air.
   4. Measure the entrained and/or dissolved gas plus volume of the instrument 100' after the aeration of the sample 8 by drawing off the air in the instrument 100' under high vacuum with the vacuum pump and measuring it with the volume measuring device 40.
   5. Determine the entrained/dissolved gas volume.

Of course, although the volume of the instrument 100' without aerating the sample 8 is described as having been obtained before commencement of aeration, it may be obtained after aeration and drawing off of any entrained/dissolved gas in the liquid sample 8.

The actual temperature of testing selected was 30° C.

The pressure of measuring the volume of air by employing the volume measuring device 40 after the vacuum pump outlet was ambient atmospheric pressure.

Test Oils

The aforementioned reference oils, F-100 and F-200, were employed as the sample 8.

Results and Observations Concerning the Study Using Protocol B

The volume of entrained/dissolved air released and measured by Protocol B for the two reference oils were as follows:

| | |
|---|---|
| F-100: | 1-mL volume. |
| F-200: | 3-mL volume. |

Note that under Protocol A testing, these oils gave the following volumes of foam (generated under the aforementioned elevated temperature selected):

| | |
|---|---|
| F-100: | 40-mL volume. |
| F-200: | 230-mL volume. |

This shows that there is a general correlation between values obtained for these reference oils under Protocols A and B.

The time of testing of Protocol B, however, is even shorter than that for Protocol A.

Some Further Reflections on Protocols A and B

Protocol A testing relates to a propensity of a liquid to foam. Proposal B testing does not employ the propensity of a liquid to foam; rather it reflects measurement of a liquid to entrain and/or dissolve a gas independent of any foaming.

The propensity of a liquid to foam may not necessarily be related to its propensity to entrain and/or dissolve a gas. Foam formation, as such, can be a highly complex phenomenon, which would relate to the liquid and the gas employed. Surface tension, temperature, size of gas streams from a porous frit, pressure, and so forth, which are encountered, may have a significant effect on foaming. Accordingly, both Protocols A and B may provide insight into properties of the sample under consideration.

Recapitulation/Elaboration of General Provisions

Accordingly, provided hereby is method for testing a liquid for aeration, entrainment and/or dissolution of a gas and/or foaming, which comprises the following steps:
   providing a sample of the liquid;
   aerating the sample with the gas for a predetermined length of time at a predetermined rate of flow of the gas, temperature and pressure;
   applying a vacuum to the aerated sample, which is held at a predetermined temperature; and
   measuring and determining gas entrained and/or dissolved in the liquid;
wherein the method embraces as part whereof at least one characteristic, parameter and/or step selected from the group, "A" and "B," as follows:
   (A) the temperature of the aerating and the measuring and determining steps are substantially elevated with respect to the liquid, and foaming of the sample is measured as part of the measuring and determining step, which foaming is engendered through application and maintenance of reduced pressure; and
   (B) the temperature of the aerating and the measuring and determining steps are moderate with respect to the liquid, and the measuring and determining step is carried out through application of reduced pressure to the sample and measurement of the gas thus drawn off.

Within the foregoing to include the "A" group above can be found one or more characteristics, parameters and/or steps of the aforementioned Protocol A, to include A1 and A2, and within the foregoing to include the "B" group above can be found one or more characteristics, parameters and/or steps of the aforementioned Protocol B. A temperature that is substantially elevated with respect to the liquid depends on human experience and such phenomena as lower and upper transition points or ranges of the liquid, which may in general be or be akin to freezing and boiling, and this temperature would typically be substantially closer to the higher transition than would the moderate temperature, although not necessarily approaching the higher transition. For example, the substantially elevated temperature of an engine oil could be, say, about from 100° C. to 200° C. or higher, for example, about 150° C. A temperature that is moderate with respect to the liquid would be below temperatures that, when considering human experience and such phenomena as the lower and upper transition points or ranges of the liquid, are considered below the elevated with respect to the liquid, typically being closer to the lower transition than the elevated temperature although not necessarily approaching the lower transition of the liquid. For example, the moderate temperature of that engine oil could be, say, about from 0° C. or lower to less than about 100° C., which would include to about 75° C. and to about 50° C. or to about 40° C., for instance, about room temperature (20° C. or 25° C.) or above to include, for example, about 30° C. Of course, corresponding substantially elevated and moderate temperatures could be lower for some substances that form liquids typically at ambient pressure, for example, light viscosity machine oil, and so forth, and could be higher with others, for example, a high viscosity gear oil, and so forth. A constant temperature may be employed throughout the testing. Differing temperatures, for instance, as in a controlled scan or in a plurality of selected discrete temperatures, may be employed.

The aforementioned apparatus or instrument is also provided.

FINAL CONCLUSION

The present invention is thus provided. Various feature(s), part(s), step(s), subcombinations(s) and/or combination(s) can be employed with or without reference to other feature(s), part(s) step(s), subcombinations(s) and/or combination(s) in its practice, and numerous and sundry adaptations and modifications can be effected within its spirit, the literal claim scope of which is particularly pointed out as follows:

I claim:

1. An apparatus useful for testing a liquid for aeration, entrainment and/or dissolution of a gas and/or foaming, which comprises an outer, selectively sealable tube, which can serve as a vessel to contain a sample of a liquid such that the sample can be tested in the vessel by aerating the sample with gas for a predetermined length of time at a predetermined rate of flow of the gas, temperature and pressure, such that a vacuum or low-pressure atmosphere can be applied to the aerated sample held at a predetermined temperature, and such that measuring and determining of gas entrained and/or dissolved in the sample can be carried out, in which the temperature of the aerating and measuring is independently at each occurrence (A) substantially elevated with respect to the liquid sample, with foaming engendered through application and maintenance of reduced pressure, and/or (B) moderate with respect to the liquid sample and lower than the substantially elevated temperature, with the measuring and determining carried out through application of reduced pressure to the sample and measurement of the gas thus drawn off; and, within the outer tube, a smaller generally vertical, inner tube also extending upward from the sealed outer tube, which smaller, inner tube is tipped at its bottom with an outlet capable of releasing a gas in a form of fine bubbles into the liquid sample—wherein:

the outer tube is transparent glass, has a sealable top portion and a hollow interior, and is of a small size such that, when the sample of the liquid is 20 mL of engine oil, the outlet capable of releasing gas of the inner tube is well below the surface of the 20-mL liquid sample to assure sufficient liquid for formation of foam;

a stopper is provided for sealing cooperation with the sealable top portion of the outer tube, which includes:

a gas inlet, which has a first valve to control or shut off introduction of the gas into the inner tube for release into the outer tube; and a gas outlet, which has a second valve to control or shut off exit of the gas, with the second valve including first and second ports for flow of the gas from the second valve, with the first port for exit of gas left over during its introduction and the second port for drawing a vacuum or otherwise providing a low-pressure atmosphere to the hollow interior of the hollow tube; and the apparatus further comprises:

a source of vacuum or low-pressure atmosphere in communication with the second port of the second valve; and a volume measuring device in communication with the second valve for ascertaining volume of released gas in conjunction with the source of vacuum or low-pressure atmosphere by direct measurement.

2. The apparatus of claim 1, wherein the outer, selectively sealable tube has an effective inside diameter of 0.7 inch and an effective inside height of twelve inches.

3. A method for testing a liquid for aeration, entrainment and/or dissolution of a gas and/or foaming, which comprises:

providing an apparatus embracing an outer selectively sealable tube, which can serve as a vessel to contain a sample of a liquid to be tested, and, within the outer tube, a smaller, generally vertical, inner tube also extending upward from the sealed outer tube, which smaller, inner tube is tipped at its bottom with an outlet capable of releasing gas in a form of fine bubbles into the liquid sample—wherein:

the outer tube is transparent glass, has a sealable top portion and a hollow interior, and is of a small size such that, when the sample of the liquid is 20 mL of engine oil, the outlet capable of releasing gas of the inner tube is well below the surface of the 20-mL liquid sample to assure sufficient liquid for formation of foam;

a stopper is provided for sealing cooperation with the sealable top portion of the outer tube, which includes:

a gas inlet, which has a first valve to control or shut off introduction of the gas into the inner tube for release into the outer tube; and a gas outlet, which has a second valve to control or shut off exit of the gas, with the second valve including first and second ports for flow of the gas from the second valve, with the first port for exit of gas left over during its introduction and the second port for drawing a vacuum or otherwise providing a low-pressure atmosphere to the hollow interior of the hollow tube; and the apparatus further embraces:

a source of vacuum or low-pressure atmosphere in communication with the second port of the second valve; and a volume measuring device in communication with the second valve for ascertaining volume of released gas in conjunction with the source of vacuum or low-pressure atmosphere by direct measurement;

providing a sample of the liquid to the apparatus;

aerating the sample with the gas released through said outlet for a predetermined length of time at a predetermined rate of flow of the gas, temperature and pressure;

applying a vacuum or low-pressure atmosphere to the aerated sample, which is held at a predetermined temperature; and measuring and determining gas entrained and/or dissolved in the liquid—wherein the method further comprises as part whereof at least one characteristic, parameter and/or step selected from the groups, "A" and "B," as follows:

(A) the temperature of the aerating and the measuring and determining steps is independently at each occurrence substantially elevated with respect to the liquid, and foaming of the sample is measured as part of the measuring and determining step, which foaming is engendered through application and maintenance of reduced pressure; and (B) the temperature of the aerating and the measuring and determining steps is independently at each occurrence moderate with respect to the liquid and lower than the temperature of the characteristic, parameter and/or step "A," and the measuring and determining step is carried out through application of reduced pressure to the sample and measurement of the gas thus drawn off.

4. The method of claim 3, wherein the outer, selectively sealable tube has an effective inside diameter of 0.7 inch and an effective inside height of twelve inches.

5. The method of claim 3, wherein the measuring and determining gas entrained and/or dissolved in the liquid is done directly by volume.

6. The method of claim 3, wherein foam from the liquid sample is generated under vacuum or low-pressure atmosphere.

7. The method of claim 3, wherein foam volume and time of foam collapse are measured of the foam generated from the liquid sample.

8. The method of claim 7, wherein a plurality of foam volume and foam collapse measurements are taken.

9. The method of claim 3, wherein the substantially elevated temperature of group "A" is about from 100° C. to 200° C., and the moderate temperature of group "B" is about from 0° C. to 75° C.

10. The method of claim 9, wherein the liquid is an engine oil.

11. The method of claim 10, wherein the gas is air.

12. The method of claim 11, wherein the engine oil sample is about 20 mL; the substantially elevated temperature of group "A" is about 150° C., and the moderate temperature of group "B" is about from 20° C. to 30° C.

13. The method of claim 3, wherein the liquid is an oleaginous liquid.

14. The method of claim 3, wherein the gas is air.

* * * * *

UNITED STATES PATENT AND TRADEMARK OFFICE
CERTIFICATE OF CORRECTION

PATENT NO. : 8,490,464 B1  
APPLICATION NO. : 12/657490  
DATED : July 23, 2013  
INVENTOR(S) : Theodore W. Selby Page 1 of 1

It is certified that error appears in the above-identified patent and that said Letters Patent is hereby corrected as shown below:

On the Title page, Related U.S. Application Data paragraph No. 60 should read as follows:

(60) Provisional application No. 61/205,658 filed on Jan. 22, 2009, provisional application No. 61/278,380 filed on Oct. 6, 2009.

In the Specification

In column 1, line 5, "61/278,370" should read "61/278,380."

Signed and Sealed this  
Seventeenth Day of September, 2013

Teresa Stanek Rea  
*Deputy Director of the United States Patent and Trademark Office*